(12) United States Patent
Choi et al.

(10) Patent No.: US 6,569,972 B1
(45) Date of Patent: May 27, 2003

(54) PHOTO-ALIGNMENT MATERIALS FOR LIQUID CRYSTAL ALIGNMENT FILM

(75) Inventors: Hwan Jae Choi, Daejun-shi (KR); Jong Lae Kim, Seoul (KR); Eun Kyung Lee, Seoul (KR); Joo Young Kim, Daejun-shi (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/207,381

(22) Filed: Jul. 30, 2002

(30) Foreign Application Priority Data

Jul. 31, 2001 (KR) ............................................. 01-46314

(51) Int. Cl.⁷ .............................................. C08F 122/40
(52) U.S. Cl. ........................ 526/262; 526/245; 526/255; 526/259; 526/260; 526/268; 526/281; 526/313; 526/328.5
(58) Field of Search .................................. 526/245, 255, 526/259, 260, 262, 268, 281, 313, 328.15

(56) References Cited

U.S. PATENT DOCUMENTS

| 5,464,669 A | | 11/1995 | Kang et al. .................... 428/1 |
| 5,578,697 A | * | 11/1996 | Kawamonzen et al. ...... 528/353 |
| 6,001,277 A | * | 12/1999 | Ichimura et al. ......... 252/299.4 |

* cited by examiner

*Primary Examiner*—Helen L. Pezzuto
(74) *Attorney, Agent, or Firm*—Lee & Sterba, P.C.

(57) ABSTRACT

A photo-alignment material useful in liquid crystal alignment films comprises a maleimide-based repeating unit and at least one additional repeating unit, or a maleimide-based repeating unit and at least two additional repeating units. The photo-alignment materials have freely-controllable pretilt angles, and they provide a display quality equivalent or superior to alignment materials made using the conventional rubbing process.

7 Claims, No Drawings

PHOTO-ALIGNMENT MATERIALS FOR LIQUID CRYSTAL ALIGNMENT FILM

BACKGROUND OF THE INVENTION

1. Field of the Invention

The present invention relates to photo-alignment materials useful in liquid crystal alignment films. More particularly, the present invention relates to photo-alignment materials useful in liquid crystal alignment films in which the pretilt angle of the materials is freely controllable while providing a display quality equivalent or superior to alignment materials made using the conventional rubbing process.

2. Description of the Related Art

The arrangement of liquid crystals in a liquid crystal display device changes in accordance with an electric field induced by an externally applied voltage. Such changes in the alignment of the liquid crystals determine whether external light entering the liquid crystal device is blocked or transmitted. Thus, the liquid crystal device can be driven by this property of the liquid crystals. The quality of a liquid crystal display device as a display device is determined by properties that are varied according to the alignment state of the liquid crystals, including light transmittance, response time, viewing angle, contrast ratio, and the like. Therefore, it is very important to uniformly control the liquid crystal alignment in liquid crystal devices.

An alignment film typically refers to a layer of polymer material, which is formed between liquid crystals, and a transparent conductive film made of indium tin oxide in order to produce the uniform alignment, i.e., orientation of liquid crystalline molecules. After formation, the polymer layer typically is subjected to a mechanical process, such as rubbing and the like, and other processes to control the alignment of liquid crystals.

The method currently used to achieve uniform alignment of liquid crystals or to orient liquid crystals in a given direction in preparing liquid crystal display devices involves disposing a layer of polymer, such as polyimide, on a transparent conductive glass substrate, and then rubbing the polymer surface at a high speed with a rotating roller that is wrapped with a rubbing cloth made of nylon or rayon. By this rubbing process, the liquid crystalline molecules are oriented with a specific pretilt angle on the surface of the alignment film.

Since this rubbing process is substantially the only method to orient liquid crystals easily and stably, most manufacturers producing liquid crystal display devices generally use the rubbing process for mass-production. However, the rubbing process has problems in that it creates scratches on the surface of the liquid crystal alignment film due to mechanical rubbing, and it generates static electricity which leads to destruction of thin film transistors. In addition, micro fibers released from the rubbing cloth may cause defects in the liquid crystal devices. Accordingly, this rubbing process reduces the production quality of the devices. A new alignment technique has been proposed that aligns liquid crystals by irradiation of light, for example, UV rays, in order to overcome the problems involved in the rubbing process as described above, and thereby to improve productivity.

Recently, liquid crystal displays have become large-scale, and the applications of the liquid crystal display are expanding beyond personal applications, such as notebook computers, to household applications, such as wall-mounted TVs. In accordance with this trend, a high quality picture and a wide viewing angle are required for the liquid crystal display devices. Also, in order to meet such demands for qualities of the liquid crystal display, the photo-alignment method is currently in the spotlight.

However, the photo-alignment methods reported by M. Schadt et al. (Jpn. J. Appl. Phys., Vol. 31, 1992, 2155), Dae S. Kang et al. (U.S. Pat. No. 5,464,669), and Yuriy Reznikov (Jpn. J. Appl. Phys., Vo. 34, 1992, L1000) are not yet commercialized, in spite of the superiority of its concept, because there is difficulty in developing novel materials to support these methods. One of the major reasons for the difficulty is that raw materials of the alignment films are not sufficiently processible to be applied to the conventional method for manufacturing liquid crystal display devices. Also, the display device using the alignment film formed by photo-alignment is inferior in display quality, as compared to the display device formed using an alignment film of polyimide by rubbing process.

Currently, the display quality of the liquid crystal display devices is increasingly enhanced and these liquid crystal display devices are recognized as display devices having the best picture quality. There also are efforts to enhance color reproducibility for the purpose of promoting the development of the liquid crystal display devices in various fields. The color reproducibility can be facilitated by improving the function of the alignment film. To this end, appropriate control of the pretilt angle of liquid crystals has become the focus of much research. So far, the pretilt angle of liquid crystals has been increased from a level of from about 1~3° to a level of from about 3~5°. In order to realize more natural color, it is desirable to raise the pretilt angle to about 7° or higher.

Typically used alignment materials made using the rubbing process, however, have a pretilt angle of from about 3~5°. When the pretilt angle is higher or lower than the aforementioned values, the aligning character is weakened relatively or faults may occur due to scratches on a surface. More specifically, though the pretilt angle is increased, it is difficult to attain a stable pretilt angle throughout the entire surface of a screen and partial nonuniformities may be observed. In addition, it is considered to be very difficult to increase the pretilt angle without deterioration of other display quality. Thus, new materials that satisfy the above conditions are required.

The disadvantages and deleterious properties described above with reference to certain materials, devices, methods, and apparatus is not intended to limit the present invention. Indeed, certain features of the invention may include any or all of the materials, devices, methods, and apparatus, without suffering from the disadvantages and deleterious properties so described.

SUMMARY OF THE INVENTION

A feature of an embodiment of the present invention is to provide a novel alignment material useful in a liquid crystal alignment film in which the pretilt angle of the alignment material is freely controllable within the range of from about 1~10°. The materials of the invention provide a display quality equivalent or superior to the alignment materials made using the conventional rubbing process.

In accordance with one feature of an embodiment of the present invention, there are provided photo-alignment materials useful in liquid crystal alignment films comprising a repeating unit represented by the following formula 1 and at least one repeating unit selected from the structures represented by the following formula 8, wherein at least 20% of the repeating units contain at least one photo-reactive functional group selected from the structures represented by the following formula 5:

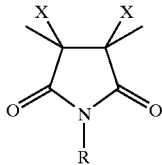
(1)

in which X is a hydrogen atom, fluorine atom, chlorine atom, or $C_{1\sim18}$ linear or branched alkyl group; Y is an oxygen atom or $C_{2\sim18}$ alkylene group; and R is a functional group having a structure represented by the following formula 3:

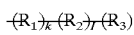
(3)

in which $R_1$ is at least one of the functional groups represented by the following formula 4; $R_2$ is at least one of the functional groups represented by the following formulas 5 and 6; $R_3$ is at least one of the functional groups represented by the following formula 7; k is an integer of from 0 to 3; I is an integer of from 0 to 5; and if there exist a plurality of $R_1$ or $R_2$, each $R_1$ or $R_2$ may be same or different:

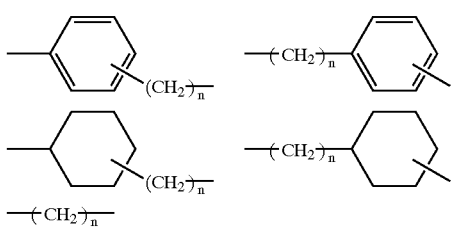
(4)

in which n is an integer of from 0 to 10,

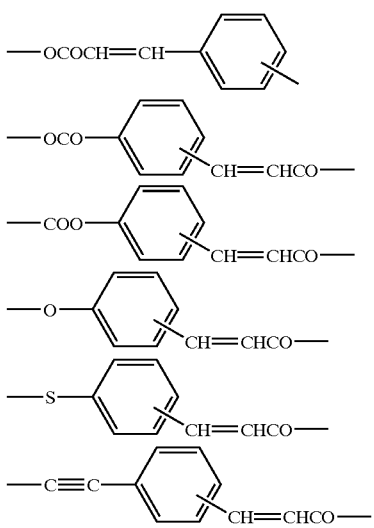
(5)

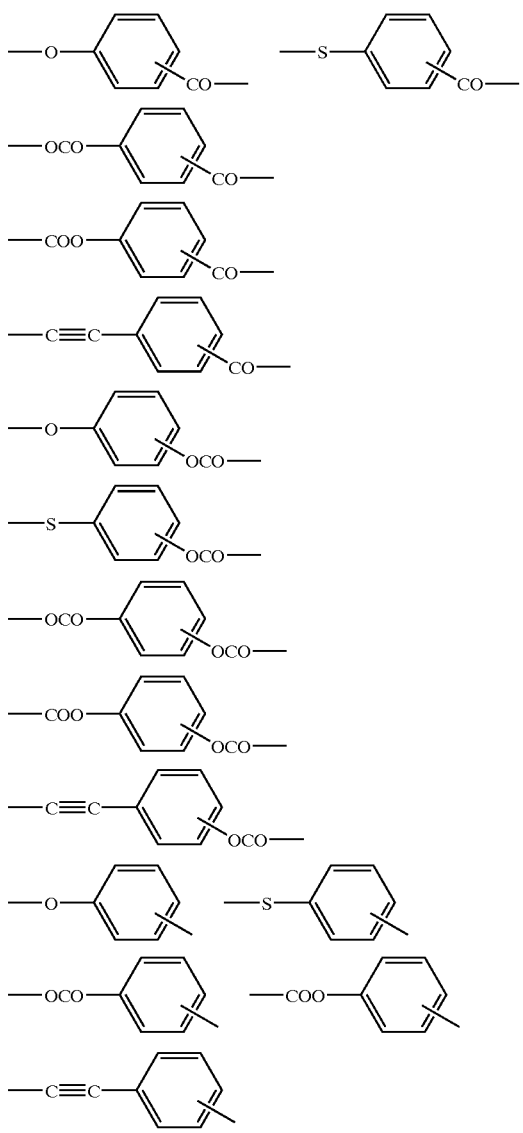
(6)

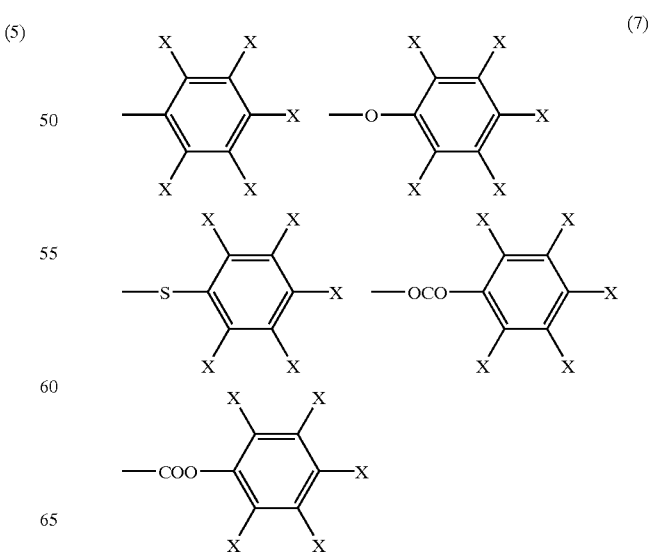
(7)

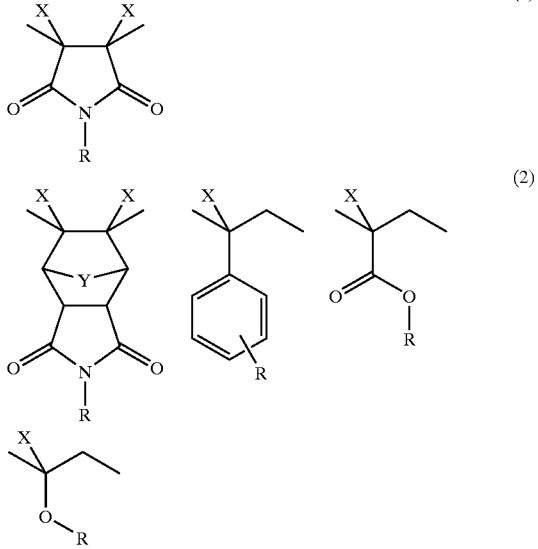

(1)

(2)

in which X is a hydrogen atom, fluorine atom, chlorine atom, or $C_{1\sim14}$ linear or branched alkyl group; Y is an oxygen atom or $C_{2\sim14}$ alkylene group; and R is a functional group having a structure represented by the following formula 3:

$$-(R_1)_k-(R_2)_l-(R_3)$$  (3)

in which $R_1$ is at least one of the functional groups represented by the following formula 4; $R_2$ is at least one of the functional groups represented by the following formulas 5 and 6; $R_3$ is at least one of the functional groups represented by the following formula 7; k is an integer of from 0 to 3; l is an integer of from 0 to 5; and if there exist a plurality of $R_1$ or $R_2$, each $R_1$ or $R_2$ may be same or different:

(4)

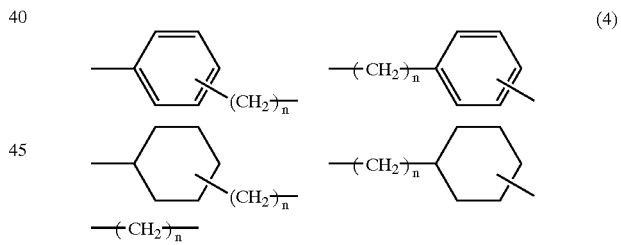

in which n is an integer of from 0 to 10,

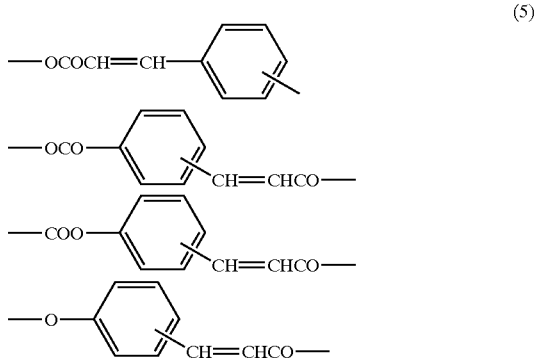

(5)

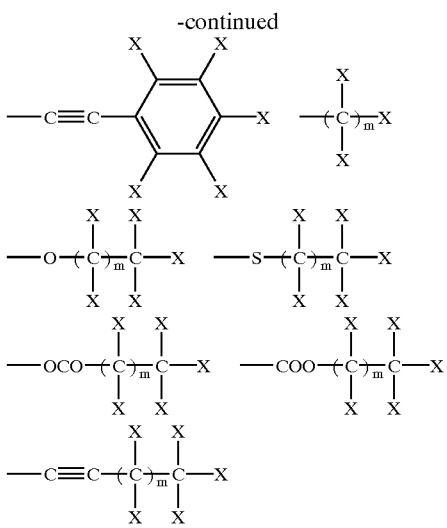

in which X in the functional groups represented by formula (7) is a hydrogen atom, fluorine atom, chlorine atom, $C_{1\sim13}$ alkyl or alkoxy group, or $-(OCH_2)_pCH_3$ in which p is an integer of from 0 to 12, and m is an integer of from 0 to 18;

(8)

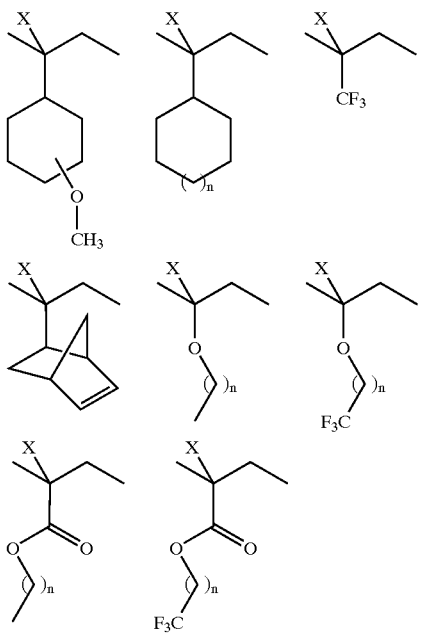

in which n is an integer of from 1 to 12.

According to another feature of an embodiment of the present invention, there are provided photo-alignment materials useful in liquid crystal alignment films comprising a repeating unit represented by the following formula 1, at least one repeating unit selected from the structures represented by the following formula 2, and at least one repeating unit selected from the structures represented by the following formula 8, wherein at least 20% of the repeating units contain at least one photo-reactive functional group selected from group consisting of structures represented by the following formula 5:

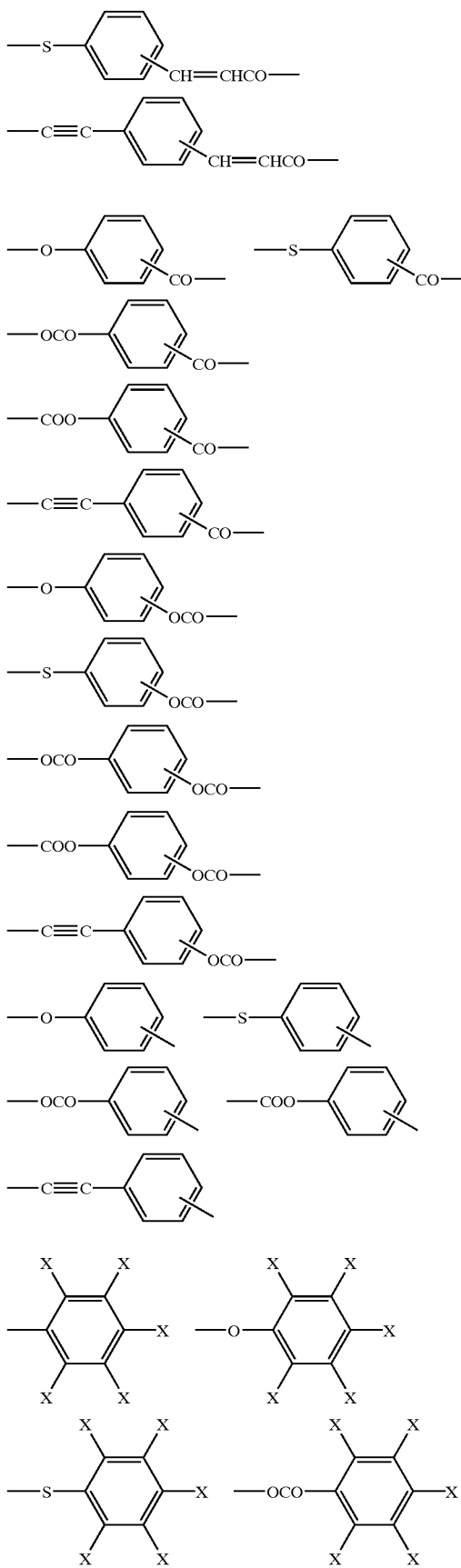

(6)

(7)

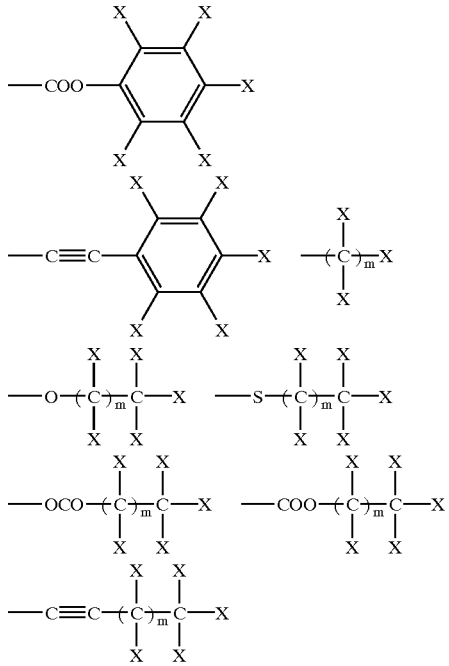

in which X in the functional groups represented by formula (7) is a hydrogen atom, fluorine atom, chlorine atom, $C_{1\sim13}$ alkyl or alkoxy group, or —$(OCH_2)_pCH_3$ in which p is an integer of from 0 to 12, and m is an integer of from 0 to 18;

(8)

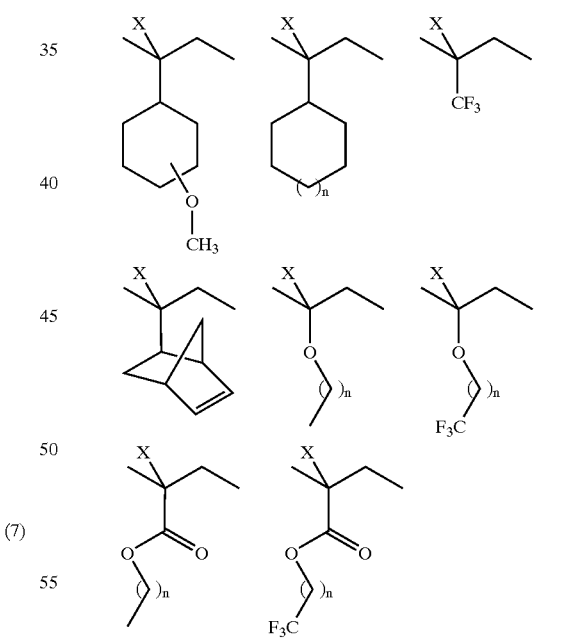

in which n is an integer of from 1 to 12.

DETAILED DESCRIPTION OF THE PREFERRED EMBODIMENTS

Priority document Korean Patent Application No. 2001-46314, filed Jul. 31, 2002, is incorporated by reference herein in its entirety.

The photo-alignment material according to the present invention includes a maleimide-type copolymer comprising at least one material having a small surface energy incorporated into the structure of the basic polymer chain. The small surface energy can be incorporated by including, for example, an aliphatic monomer, particularly a cycloaliphatic monomer or fluorinated monomer, in order to freely control the pretilt angle. Particularly, such cycloaliphatic monomer or fluorinated monomer is characterized by not bearing a photo-reactive group. These monomers are capable of reducing the surface energy and may be substituted at a terminal position of the side chain or other positions. However, according to the present invention, the above-mentioned monomers preferably are directly attached to the polymeric main chain because this configuration more effectively accomplishes proper and free control of the pretilt angle of liquid crystals.

Therefore, the alignment material of the present invention preferably includes copolymers based on at least maleimide type monomers comprising a maleimide-based repeating unit represented by the following formula 1 and at least one repeating unit selected from the structures represented by the following formula 8, or a polymer based on at least a maleimide-based repeating unit represented by the following formula 1, at least one repeating unit selected from the structures represented by the following formula 8, and at least one repeating unit selected from the structures represented by the following formula 2:

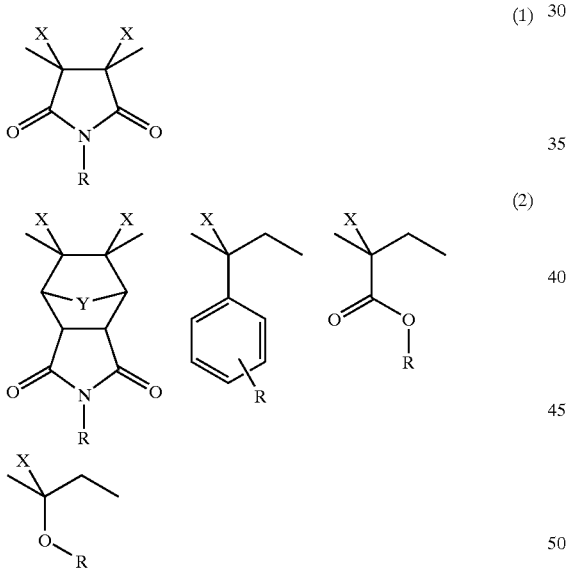

in which X is a hydrogen atom, fluorine atom, chlorine atom, or $C_{1-14}$ linear or branched alkyl group; Y is an oxygen atom or $C_{2-14}$ alkylene group; and R is a functional group having a structure represented by the following formula 3:

in which $R_1$ is at least one of the functional groups represented by the following formula 4; $R_2$ is at least one of the functional groups represented by the following formulas 5 and 6; $R_3$ is at least one of the functional groups represented by the following formula 7; k is an integer of from 0 to 3; l is an integer of from 0 to 5; and if there exist a plurality of $R_1$ or $R_2$, each $R_1$ or $R_2$ may be same or different:

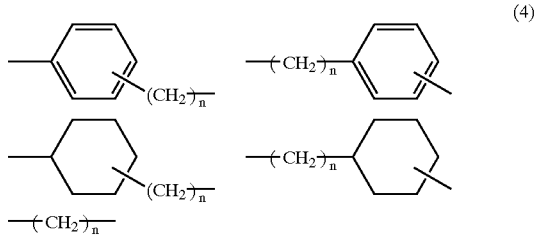

in which n is an integer of from 0 to 10,

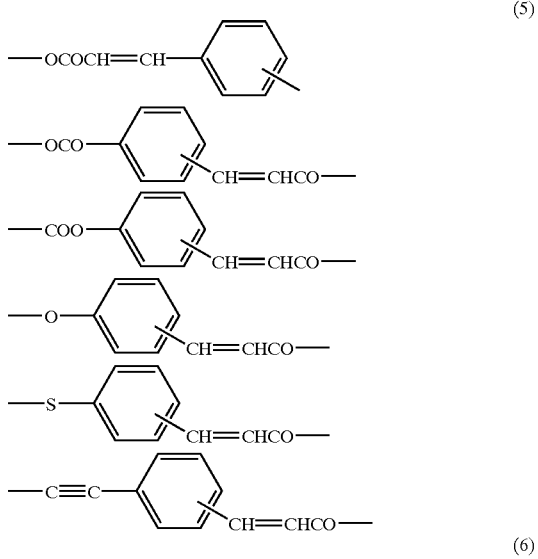

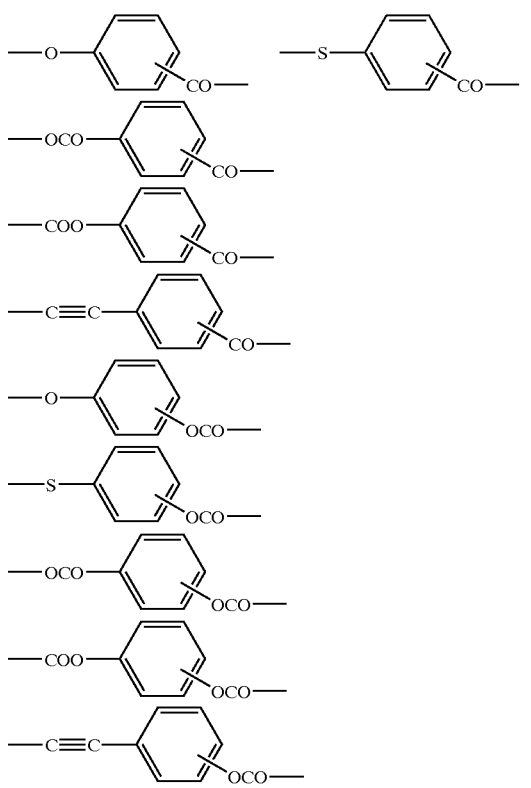

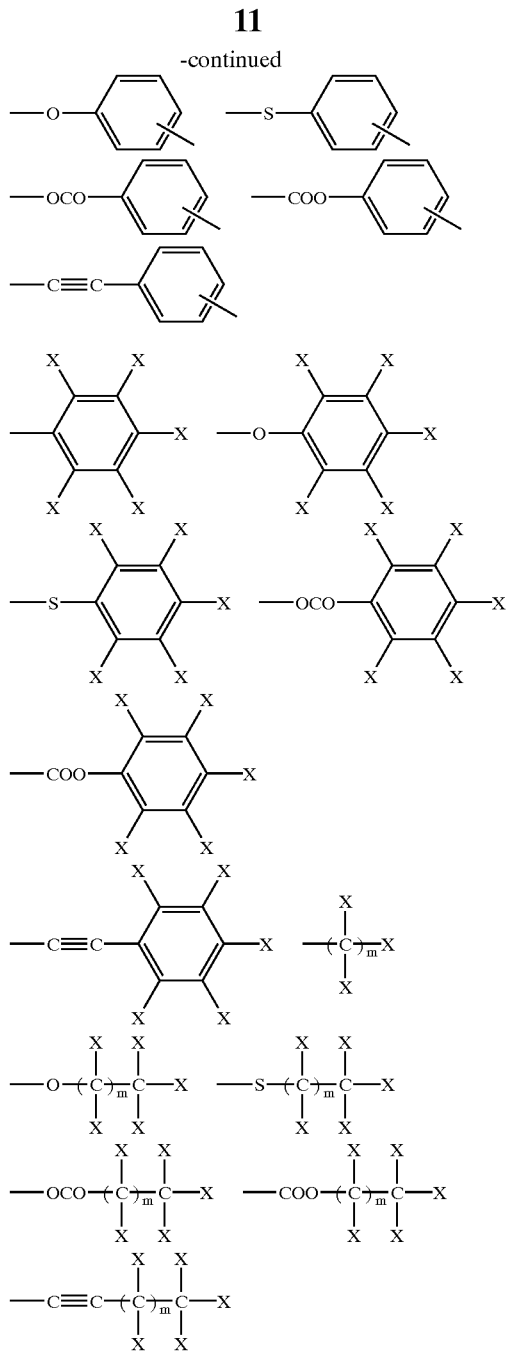

in which X in the functional groups represented by formula (7) is a hydrogen atom, fluorine atom, chlorine atom, $C_{1\sim13}$ alkyl or alkoxy group, or $-(OCH_2)_pCH_3$ in which p is an integer of from 0 to 12, and m is an integer of from 0 to 18;

(8)

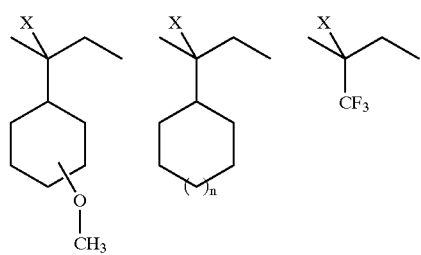

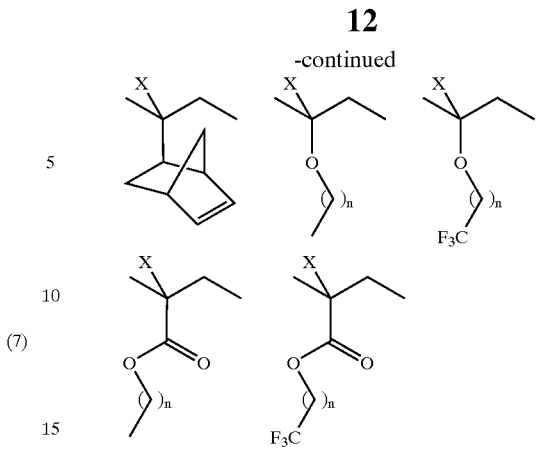

in which n is an integer of from 1 to 12.

The repeating units of formula 8 preferably do not contain a side chain R group. They can form copolymers, terpolymers, or macromers together with a maleimide-based monomer represented by the formula 1 or can form polymers together with a maleimide-based monomer represented by the formula 1, and at least one monomer represented by formula 2. By introducing such aliphatic or fluorinated monomers into the structure of the main chain, it is possible to improve the electrical properties of an alignment material and the display properties of the liquid crystal display device.

As used herein, the term "polymer" encompasses homopolymers, copolymers, terpolymers, tetrapolymers, and other macromers, and is not intended to be limited to any particular number of repeating units. Polymers also may include impurities and additives in addition to the repeating units described herein.

Preferably, the proportion of repeating units containing at least one photo-reactive group is regulated to be preferably at least 20% of the polymer, more preferably at least 30% of the polymer.

The polymer for the photo-alignment material according to the present invention preferably is dissolved in a solvent and then applied to a thin film transistor (TFT) substrate or color filter substrate in a printing method to form a photo-alignment film instead of the conventional polyimide made by the rubbing process. Thus alignment of liquid crystal can be achieved by using a 3 kW mercury lamp instead of a conventional rubbing process, in an exposing process of polarized ultra violet rays. In this process, the exposure energy typically is from about 200 to about 2,000 $mJ/cm^2$. Generally, when the exposure energy is more than 50 $J/cm^2$, the liquid crystal can be aligned. The irradiation of the ultra violet rays preferably is carried out by an inclined irradiation method, i.e., the ultra violet rays are irradiated onto the surface of the alignment film which is inclined at a given tilt angle, to induce a pretilt angle to the liquid crystal. This procedure corresponds to the process of controlling the strength and number of rubbings in the conventional rubbing process to adjust the pretilt angle.

The present invention now will be described in detail with reference to following examples. These examples however, are intended to illustrate the present invention and should not be construed as limiting the scope of the present invention.

EXAMPLES

1) Synthesis of a photo-alignment material

Example 1

Synthesis of a photo-alignment material having the following repeating unit structure:

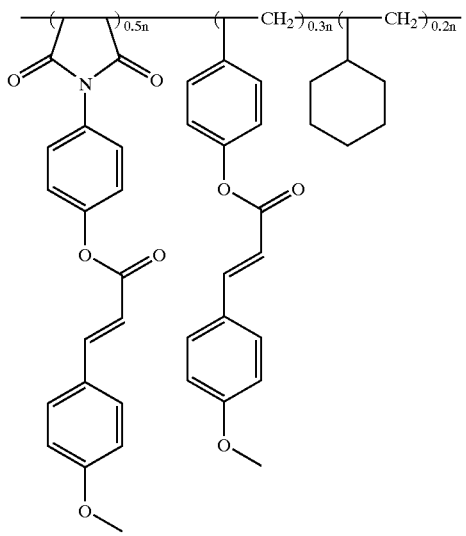

In accordance with the following reaction scheme, 10 g (0.10 mol) of maleic anhydride and 10.1 g (0.09 mol) of aminophenol were added to 100 ml of toluene and stirred for 2 hours at room temperature to produce an amic acid type intermediate. The resulting solution was added to 100 ml of acetic anhydride and dehydrated with 0.41 g (0.005 mol) of sodium acetate ($CH_3COONa$) for 4 hours at a temperature of 95° C. to produce 4-acetoxyphenyimaleimide at 50% yield.

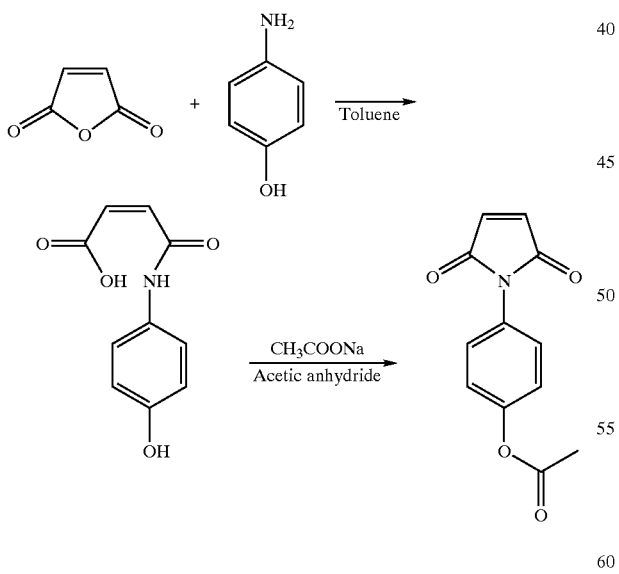

Then, 10 g (0.043 mol) of the above-syrithesized 4-acetoxyphenylmaleimide was radical-polymerized with 4.2 g (0.025 mol) of acetoxystyrene and 1.8 g (0.017 mol) of vinylcyclohexane at a temperature of 65° C. for 4 hours in acetone solvent using 0.35 g of AIBN (2,2'-azobisisobutyronitrile) as a polymerization initiator to form a terpolymer as follows.

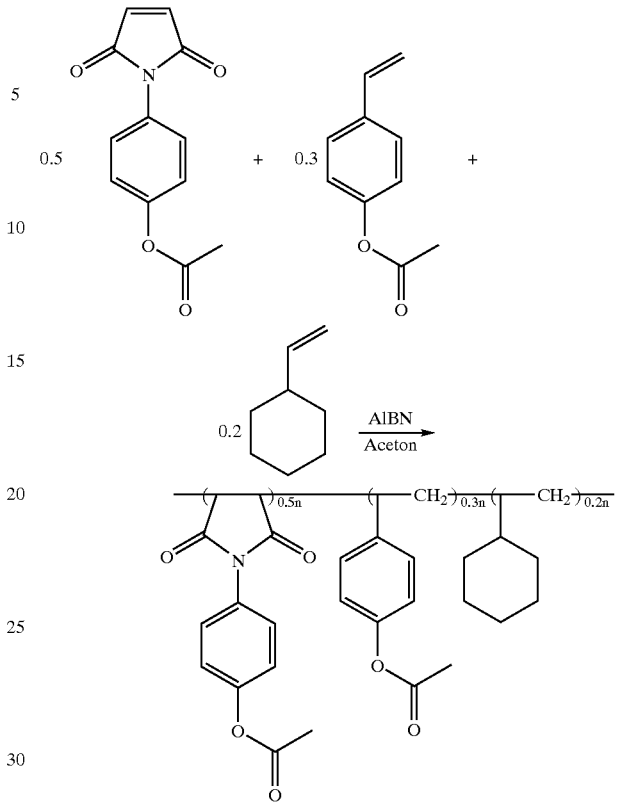

The resulting terpolymer was deprotected with 5 g of p-toluenesulfonic acid (p-TsOH) in 1 l of a mixture of methanol and acetone at a temperature of 80° C. for 5 hours to produce a polymer having the following main chain structure at 85% yield.

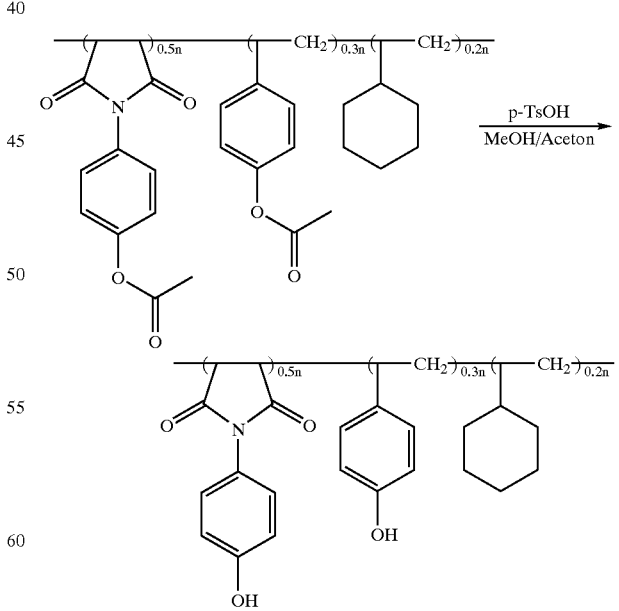

Then, 1 g (0.003 mol) of the above-synthesized polymer and 1.2 g (0.01 mol) of triethylamine were added to 20 ml of 1-methyl-2-pyrrolidinone. 4-methoxycinnamoyl chloride (1.4 g (0.007 mol)) then was added thereto and stirred at room temperature for 1 hour to yield the alignment material of the present example at 70% yield as follows.

procedure as described in Example 1 to produce a final polymer main chain having the following structure at 85% yield.

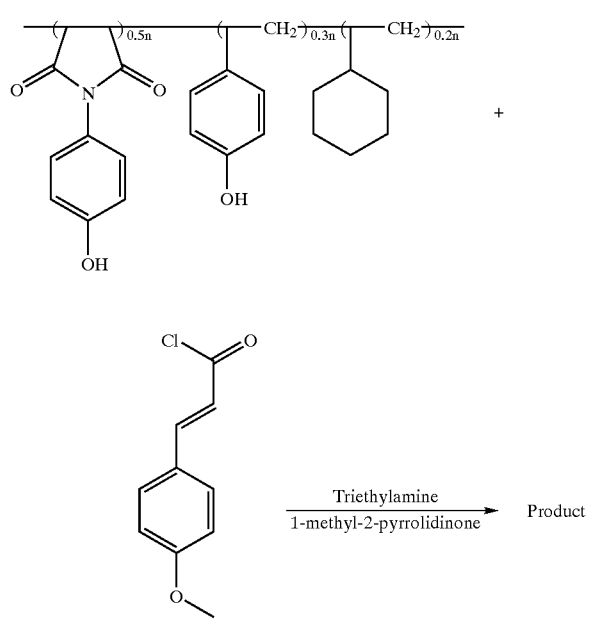

Example 2
Synthesis of a photo-alignment material having the following repeating unit structure:

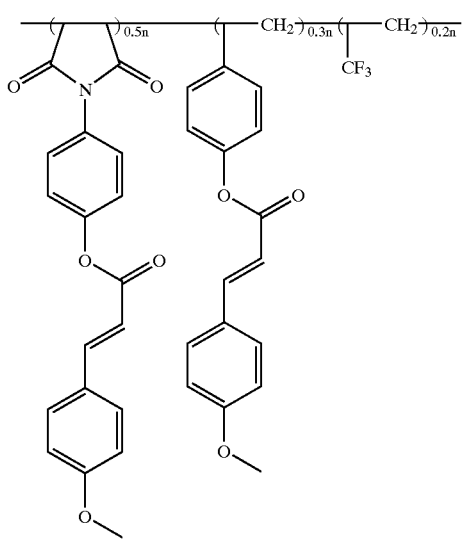

The main chain of the polymer was synthesized according to the same procedures as described in Example 1. That is, 10 g (0.043 mol) of 4-acetoxyphenylmaleimide synthesized in the same method as described in Example 1, 4.2 g (0.025 mol) of acetoxystyrene, 1.6 g (0.017 mol) of 3,3,3-trifluoropropene and 0.35 g of AIBN as a polymerization initiator were added to acetone and radical-polymerized at a temperature of 65° C. for 4 hours to form a terpolymer. The resulting terpolymer was deprotected according to the same

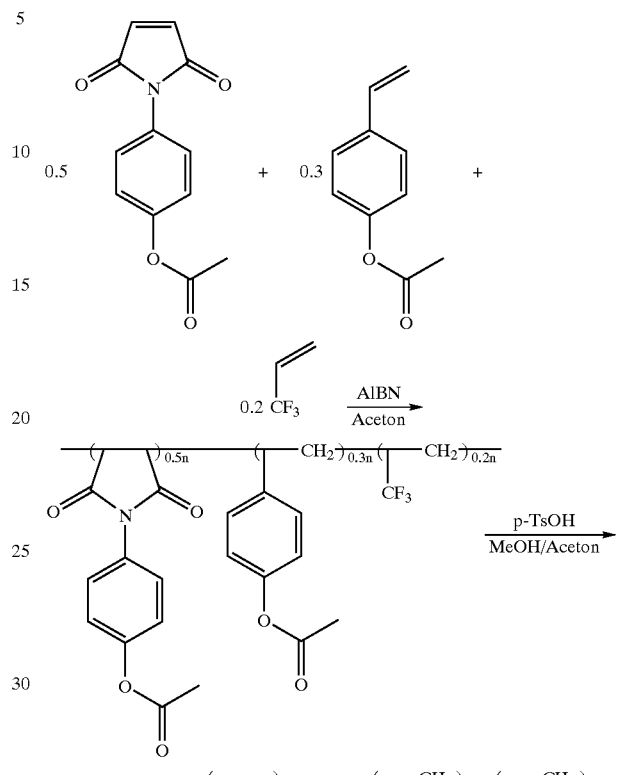

Then, 1 g (0.003 mol) of the above-synthesized polymer main chain was dissolved in 20 ml 1-methyl-2-pyrrolidinone, 1.2 g (0.001 mol) of triethylamine and 1.4 g (0.007 mole) of 4-methoxy cinnamoylchloride as a side chain then were added to the solution and stirred for 1 hour at room temperature to substitute the side chain into the main chain. The final photo-alignment material was obtained at 70% yield.

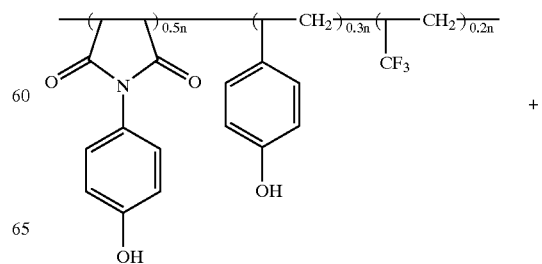

Example 3

Synthesis of a photo-alignment material having the following repeating unit structure:

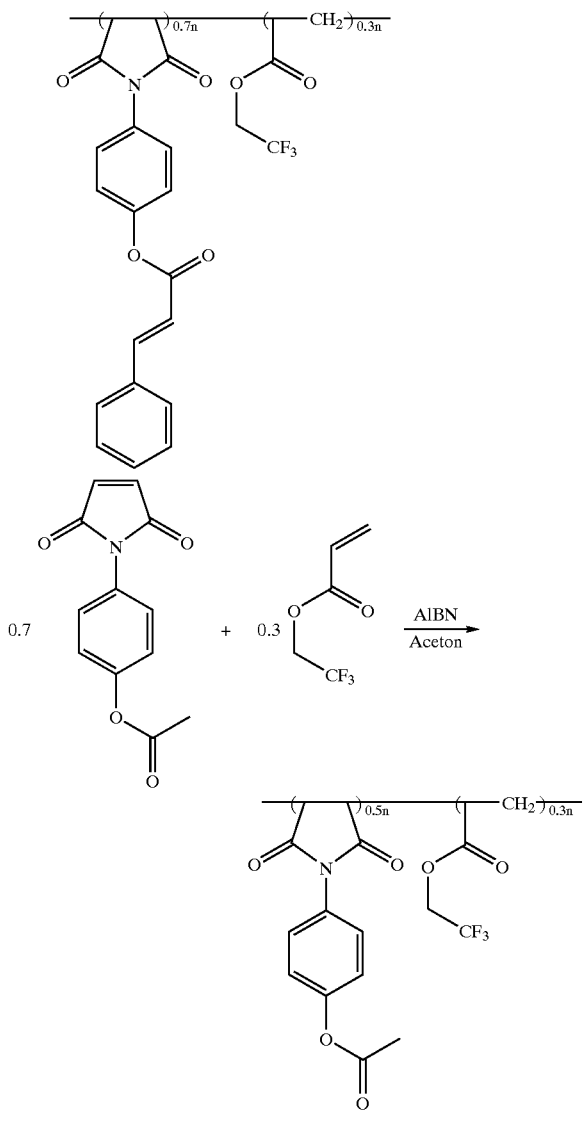

The main chain of the polymer was synthesized according to the procedures as described in Example 1. That is, 10 g (0.043 mol) of 4-acetoxyphenylmaleimide synthesized in the same method as described in Example 1, 3.2 g (0.018 mol) of trifluoroethylacrylate and 0.35 g of AIBN as a polymerization initiator were added to acetone and polymerized at a temperature of 65° C. for 4 hours to form a copolymer as follows.

The resulting copolymer was deprotected in the same procedure as described in Example 1 to yield a polymeric main chain having the following structure at 70% yield.

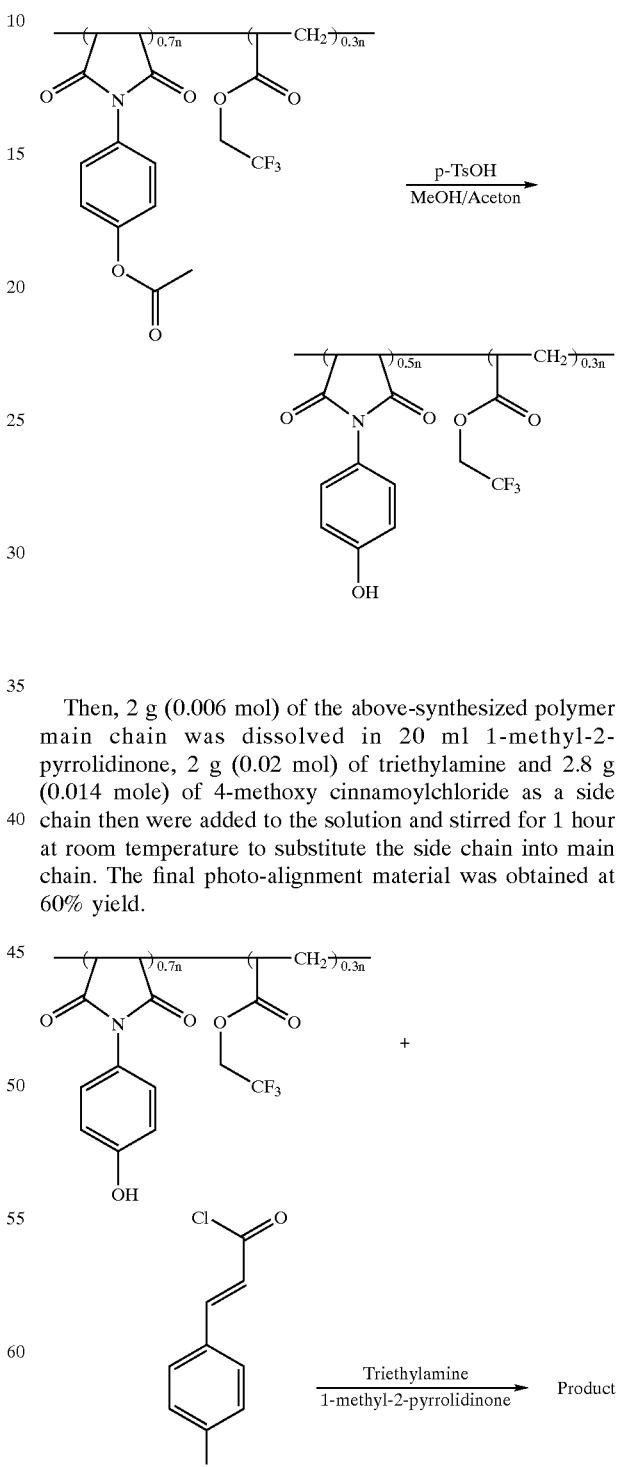

Then, 2 g (0.006 mol) of the above-synthesized polymer main chain was dissolved in 20 ml 1-methyl-2-pyrrolidinone, 2 g (0.02 mol) of triethylamine and 2.8 g (0.014 mole) of 4-methoxy cinnamoylchloride as a side chain then were added to the solution and stirred for 1 hour at room temperature to substitute the side chain into main chain. The final photo-alignment material was obtained at 60% yield.

Example 4

Synthesis of a photo-alignment material having the following repeating unit structure:

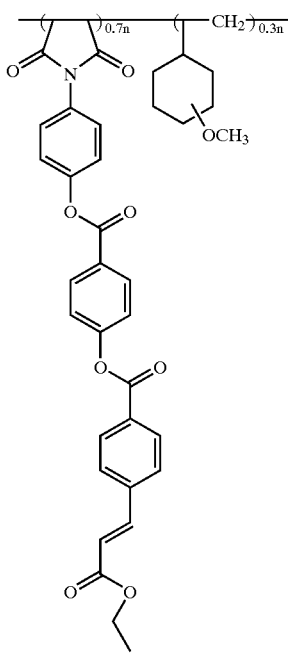

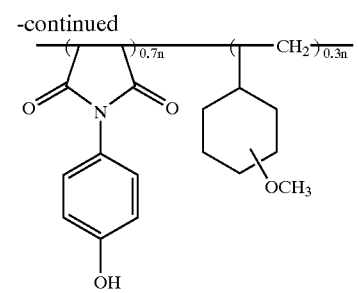

The main chain of the polymer was synthesized according to the same procedures as described in Example 1. That is, 10 g (0.043 mol) of 4-acetoxyphenylmaleimide synthesized in the same method as described in Example 1, 2.24 g (0.018 mol) of 4-vinyl-1-cyclohexene 1,2-epoxide and 0.35 g of AIBN as a polymerization initiator were added to acetone and polymerized at a temperature of 65° C. for 4 hours to form a polymer. The resulting polymer was deprotected according to the same procedure as described in Example 1 to produce a polymer main chain at 50% yield as follows.

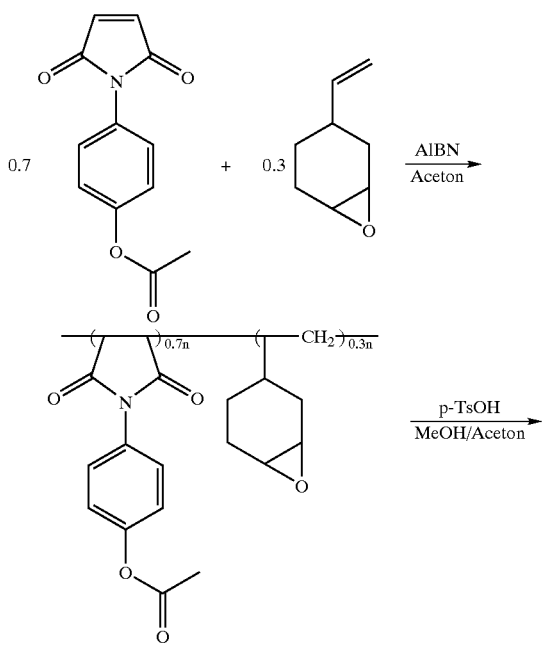

The side chain was synthesized as follows. First, 1 g (0.006 mol) of 4-carboxybenzaldehyde was reacted with 0.79 g (0.006 mol) of thionyl chloride in dichloromethane for 40 minutes and then reacted with 0.79 g (0.006 mol) of ethyimalonate in 50 ml of pyridine at a room temperature for 3 hours. The product was subsequently subjected to acyl-chlorination to produce an intermediate, ethyl-trans-chlorocarbonyl cinnamate at 50% yield. This intermediate was reacted with 0.98 g (0.006 mol) of 4-hydroxybenzoic acid in aqueous NaOH/DMSO(dimethyl sulfoxide) solution at room temperature for 2 hours to produce the side chain structure at 60% yield as follows.

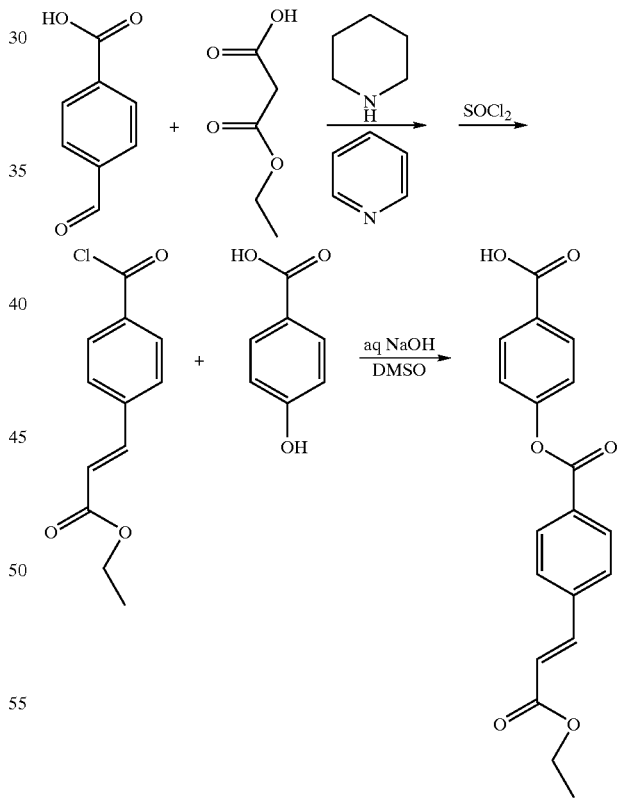

The above-synthesized side chain (4.1 g (0.01 mol)) was acyl-chlorinated. The resulting product, 1 g (0.005 mol) of the above-synthesized polymer and 2.1 g (0.02 mol) of triethylamine were dissolved in 20 ml of 1-methyl-2-pyrrolidinone and stirred for 1 hour at a room temperature.

Thus, the final alignment material was obtained at 60% yield.

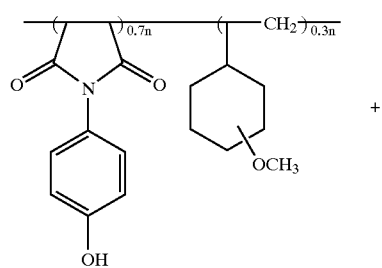

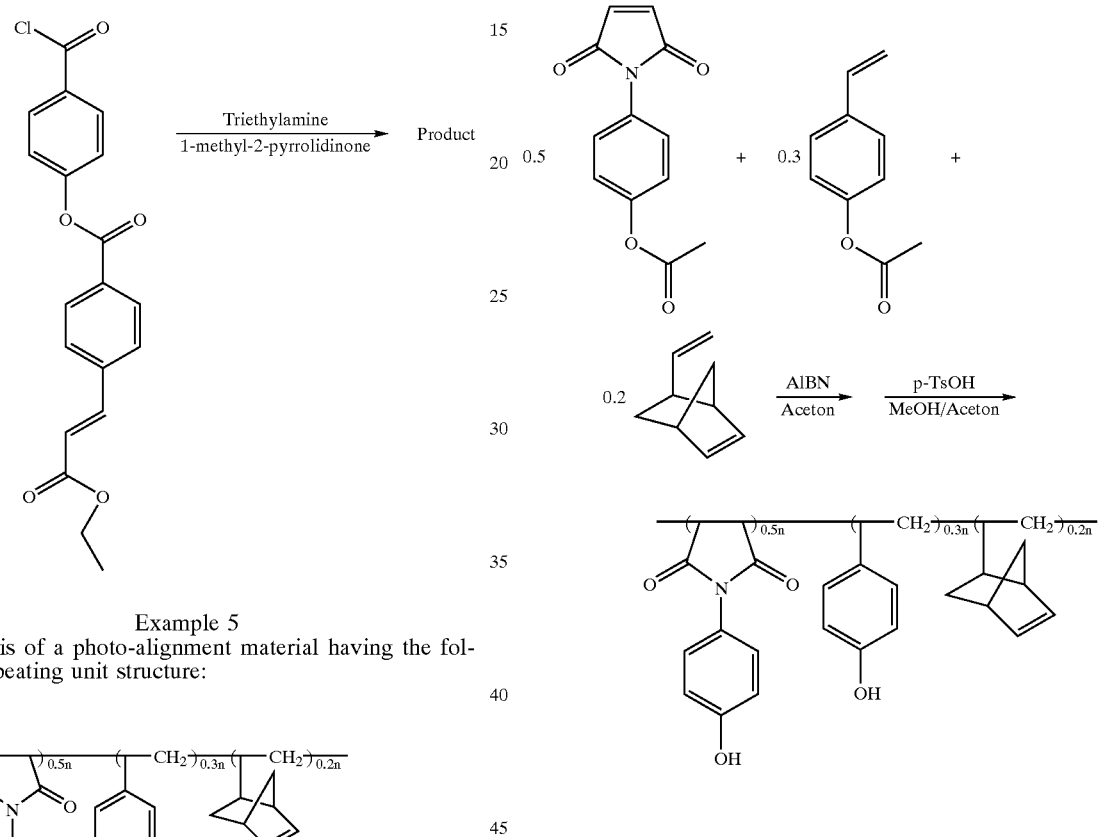

Example 5
Synthesis of a photo-alignment material having the following repeating unit structure:

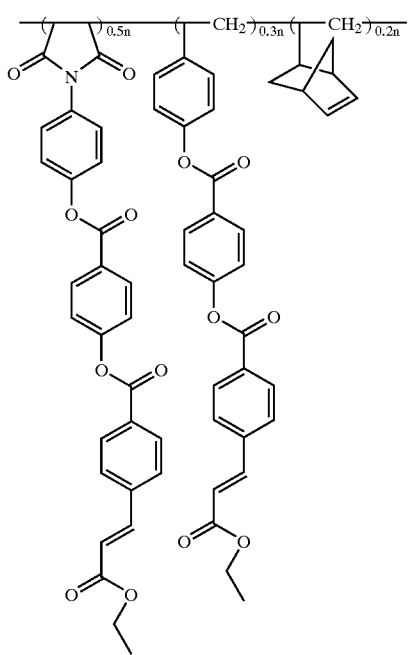

The main chain of the above polymer was synthesized according to the same procedures as described in Example 1. That is, 10 g (0.043 mol) of 4-acetoxyphenylmaleimide, synthesized in the same method as described in Example 1, 4.2 g (0.025 mol) of acetoxystyrene, 2.04 g (0.017 mol) of 5-vinyl-2-norbornene and 0.35 g of AIBN as a polymerization initiator were added to acetone, and polymerized at a temperature of 65° C. for 4 hours to form a terpolymer. The resulting terpolymer was deprotected according to the same procedure as described in Example 1 to yield a polymer main chain at 85% yield as follows.

Then, 1.7 g (0.005 mol) of side chain synthesized in the same manner as that described in Example 1, was acyl-chlorinated. The resulting product, 1 g (0.002 mol) of the polymer prepared as above and 0.73 g (0.007 mol) of triethylamine were dissolved in 20 ml of 1-methyl-2-pyrrolidinone and stirred for 1 hour at room temperature. Thus, the final alignment material was obtained at 60% yield.

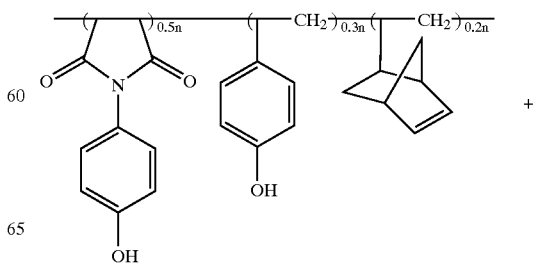

-continued

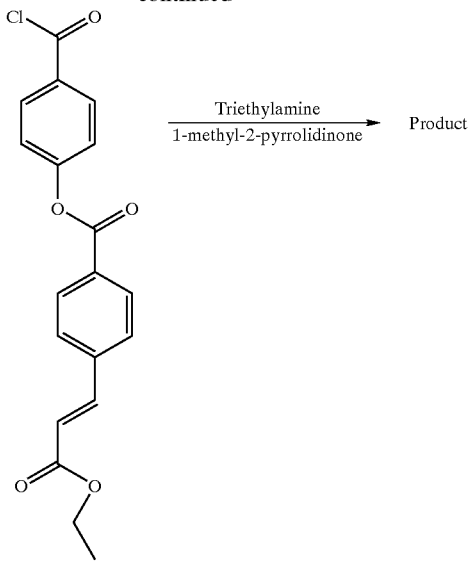

Example 6

Synthesis of a photo-alignment material having the following repeating unit structure:

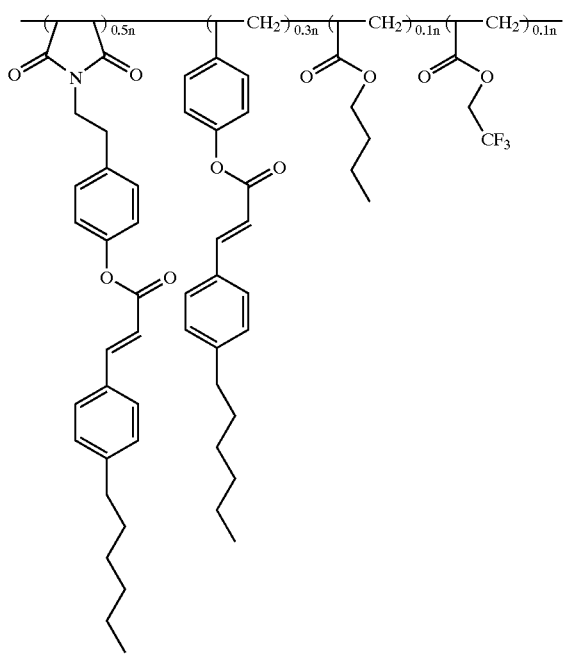

Maleic anhydride (10 g (0.1 mol)) and 13.7 g (0.1 mol) of aminoethyiphenol were added to 100 ml of toluene and stirred for 1 hour at room temperature to produce an amic type intermediate. The resulting solution was dehydrated with 4.1 g (0.05 mol) of sodium acetate at a temperature of 85° C. to produce 4-acetoxyphenylethymaleimide at 80% yield.

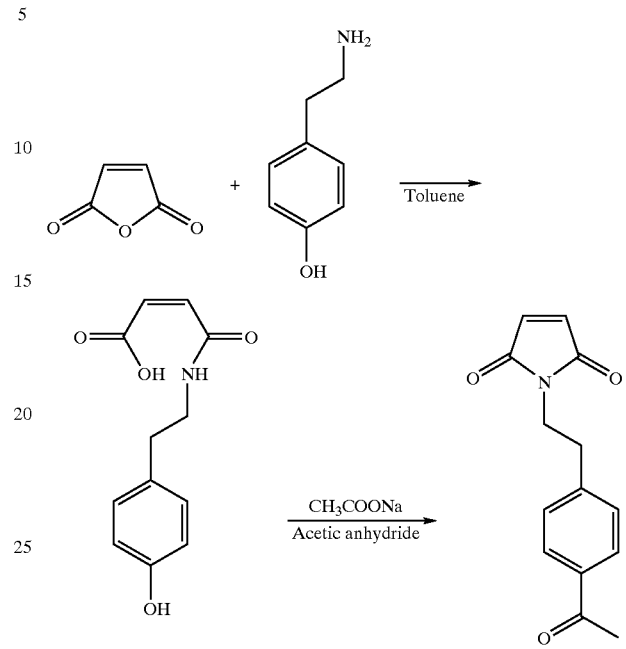

Then, 10 g of 4-acetoxyphenyiethylmaleimide synthesized above was mixed with 4-acetoxystyrene, n-butylacrylate and trifluorooxymethlacrylate in a molar equivalent ratio of 1:0.6:0.2:0.2 and added to acetone, followed by addition of 0.35 g of AIBN as a polymerization initiator. The materials were polymerized at a temperature of 65° C. The acetoxy groups of the resulting tetrapolymer were deprotected with 0.01 equivalent of p-toluenesulfonic acid in a mixture of methanol and acetone at a temperature of 80° C. for 5 hours to produce a polymer main chain having the following structure at 70% yield.

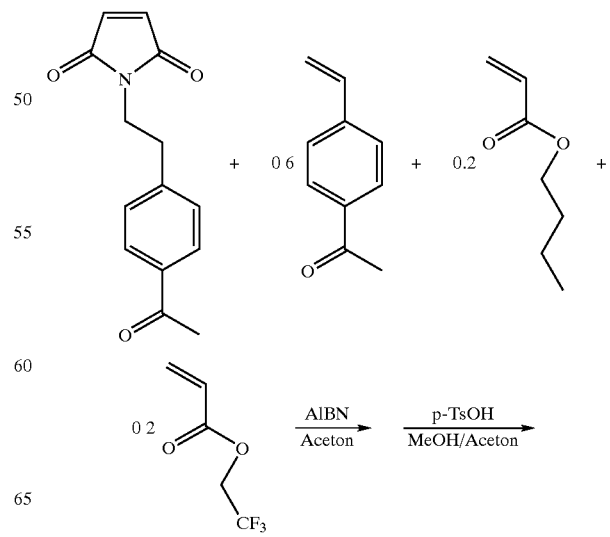

-continued

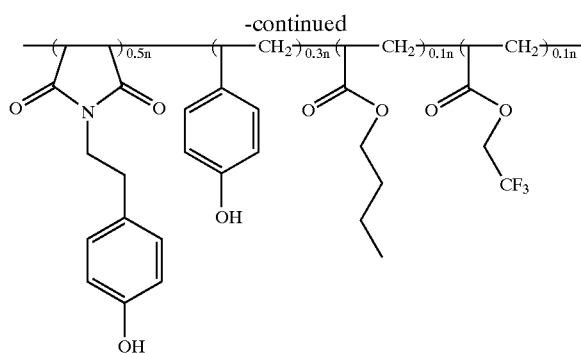

The above-synthesized polymer main chain (2 g (0.007 mol)) and 2.5 g (0.025 mol) of triethylamine were dissolved in 20 ml 1-methyl-2-pyrrolidinone. 4.7 g (0.013 mol) of 4-hexylcinnamoyl chloride was added thereto and stirred for 1 hour at a room temperature. Thus, the final alignment material was synthesized.

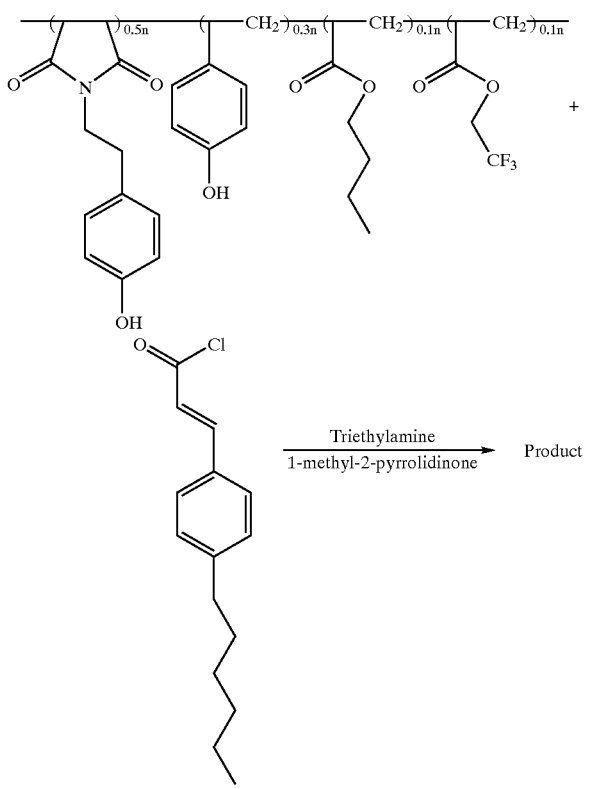

2) Preparation of liquid crystal display devices and properties assessment of the liquid crystal display devices The respective photo-alignment materials prepared in the above Examples were dissolved in a mixture of 1-methyl-2-pyrrolidinone and 2-butoxyethanol. The resulting solutions of the respective photo-alignment materials were coated on TFT substrates and color filter substrates in a printing method to form photo-alignment films. These films then were subjected to an exposing process with polarized ultra violet rays using a 3 kW mercury lamp. Fifteen inch (15") liquid crystal display devices were prepared according to the well-known process commonly used for manufacturing liquid crystal display devices. The entire procedure, except for the above exposing process to orient the liquid crystals, was carried out by commonly used processes for manufacturing liquid crystal display devices. The prepared respective 15" liquid crystal display devices then were examined for basic electrooptical properties as a display device, such as contrast ratio, response time, viewing angle and brightness. The results are shown in Table 4 below.

Unit cells (1") also were prepared using the respective photo-alignment materials from the above Examples according to the same method as above. The prepared unit cells were measured for voltage holding ratio and residual DC. The results are shown in Tables 1 and 2.

In addition, 1" unit cells using each photo-alignment materials of the above Examples were prepared. An antiparallel cell with a cell gap of 55 μm was produced in such a manner that the aligning direction of the liquid crystals of the each substrate was reversed. The respective antiparallel cells were measured for their pretilt angles according to a crystal rotation method. The results are shown in Table 3 below.

In each case, liquid crystals for TN mode TFT-LCD, supplied by Merck (N.J., USA), were used.

Comparative Example 1

Using polyimide (SE 7992, supplied by Nissan Chemicals, JP) which is widely used as a alignment material, a 15" liquid crystal display device and 1" unit cell were prepared according to the same method as described in the above inventive examples. Their electrooptical properties, voltage holding ratio and residual DC, and pretilt angle were measured and are shown in Tables 1 to 4.

Comparative Example 2

Using the photo-alignment material having the following molecular structure, as disclosed in Korean Patent Laid-open Publication No. 2000–8633, a 15" liquid crystal display device and 1" unit cell were prepared according to the same method as described in the above inventive examples. Their electrooptical properties, and voltage holding ratio and residual DC were measured and are shown in Tables 1 to 4.

TABLE 1

| Voltage holding ratio* | | |
|---|---|---|
| | Measuring Temperature | |
| | Room temperature (25° C.) | 60° C. |
| Example 1 | 97.9% | 94.7% |
| Example 2 | 99.1% | 97.5% |

TABLE 1-continued

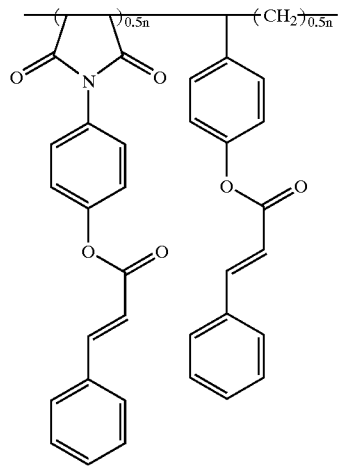

Voltage holding ratio*

| | Measuring Temperature | |
|---|---|---|
| | Room temperature (25° C.) | 60° C. |
| Example 3 | 99.5% | 98.0% |
| Example 4 | 99.0% | 96.9% |
| Example 5 | 99.1% | 95.7% |
| Example 6 | 99.3% | 97.1% |
| Comp. Example 1 | 99.1% | 95.2% |
| Comp. Example 2 | 97.5% | 92.4% |

*The voltage holding ratio was measured under the condition of 1V for 64 μs, with a frequency of 60 Hz.

TABLE 2

Residual DC*

| | Max. ΔC |
|---|---|
| Example 1 | $21.5 \times 10^{-9}$ F |
| Example 2 | $11.2 \times 10^{-9}$ F |
| Example 3 | $9.7 \times 10^{-9}$ F |
| Example 4 | $15.7 \times 10^{-9}$ F |
| Example 5 | $10.3 \times 10^{-9}$ F |
| Example 6 | $9.5 \times 10^{-9}$ F |
| Comp. Example 1 | $31.2 \times 10^{-9}$ F |
| Comp. Example 2 | $55.2 \times 10^{-9}$ F |

*The residual DC was relatively estimated by comparing the point at which the difference of electric capacitances (ΔC) at the same voltage are maximum.

TABLE 3

Pretilt angle*

| | Exposure angle | Exposure energy | Pretilt angle |
|---|---|---|---|
| Example 1 | 30° | 500 mJ/cm² | 0.7° |
| | | 1000 mJ/cm² | 1.1° |
| Example 2 | 30° | 500 mJ/cm² | 1.3° |
| | | 1000 mJ/cm² | 2.5° |
| Example 3 | 30° | 500 mJ/cm² | 4.5° |
| | | 1000 mJ/cm² | 6.2° |
| Example 4 | 30° | 500 mJ/cm² | 3.2° |
| | | 1000 mJ/cm² | 4.8° |
| Example 5 | 30° | 500 mJ/cm² | 3.4° |
| | | 1000 mJ/cm² | 5.1° |

TABLE 3-continued

Pretilt angle*

| | Exposure angle | Exposure energy | Pretilt angle |
|---|---|---|---|
| Example 6 | 30° | 500 mJ/cm² | 5.1° |
| | | 1000 mJ/cm² | 8.5° |
| Comp. Example 1 | | Rubbing depth | Pretilt angle |
| | | Normal (−1) mm | 4.6° |
| | | Normal | 4.1° |
| | | Normal (+1) mm | 3.5° |
| Comp. Example 2 | Exposure angle | Exposure energy | Pretilt angle |
| | 30° | 500 mJ/cm² | 0.3° |
| | | 1000 mJ/cm² | 0.6° |

*Measuring methods
Pretilt angle was measured by a crystal rotation method.
Rubbing depth was adjusted by increasing or decreasing the height of a rotary roller on the basis of optimized standard. (+1) mm means the case where the rubbing was performed intensively, as compared to the standard.
Exposure angle was defined as the incidence angle of irradiated beam of light to the normal vector of the substrate.
Exposure energy was determined by measuring the intensity of illumination of irradiated light having a wavelength within a range of 240 to 350 nm while varying irradiation times.

TABLE 4

Electrooptical properties of 15" TFT LCD

| | Contrast ratio* | Response time (msec) | Brightness* (cd/m²) | Viewing angle Right/Left | Viewing angle Top/Bottom |
|---|---|---|---|---|---|
| Example 1 | 198 | 31 | 204 | 58/58 | 45/>60 |
| Example 2 | 205 | 26 | 196 | 59/58 | 45/>60 |
| Example 3 | 200 | 29 | 208 | 59/58 | 45/>60 |
| Example 4 | 211 | 32 | 201 | 58/58 | 45/>60 |
| Example 5 | 210 | 30 | 205 | 59/59 | 45/>60 |
| Example 6 | 215 | 29 | 212 | 58/59 | 45/>60 |
| Comp. Example 1 | 200 | 35 | 200 | 58/58 | 45/>60 |
| Comp. Example 2 | 185 | 32 | 205 | 58/59 | 45/>60 |

*The contrast ratio and brightness are reported as average values of measurements taken at 9 different positions on the screen.

From the above Tables 1, it can be seen that the Examples 1 to 6 according to the present invention showed improvements in voltage holding ratio, particularly at 60°, when compared to alignment materials made using the rubbing process. The results of residual DC also were found to be improved in the Examples according to the present invention, when compared to the alignment material made using the rubbing process. Residual DC is an important property in terms of stability of display quality of display devices. Specifically, it is considered as a main factor associated with an image sticking phenomenon that hinders the natural display of moving images. Voltage holding ratio also is considered as an important factor involved in image sticking phenomenon, along with the Residual DC, and further is considered a critical factor related to the reliability of display devices.

From the results of pretilt angle measurement reported in Table 3, it is noted that by selecting the types of the photo-reactive substituents and varying the conditions of the exposing process, it is possible to freely control the pretilt angle of liquid crystals. The pretilt angle is believed to be an essential factor for presentation of natural color and uniform picture quality throughout the whole screen of the large-scale display, as well as the aforementioned electrooptical properties.

Generally used alignment materials made using the rubbing process have pretilt angles of from about 3~5°. When the pretilt angle of these generally used alignment materials was higher or lower than the aforementioned values, the aligning character was weakened relatively or faults occurred due to scratches on the surface. Specifically, even though the pretilt angle was increased, it was difficult to attain a stable pretilt angle throughout the entire surface of a screen and partial nonuniformities may be observed. In addition, it was considered to be very difficult to increase the pretilt angle without deterioration of other display quality.

From the results of the Examples and Comparative Examples, it was confirmed that according to the present invention, it is possible to freely control the pretilt angle to be within the range of from about 1 to about 10° by regulating the photo-reactive groups in the molecular structure of the photo-alignment material, and by simply varying the conditions of the exposing process, such as the exposure energy and angle. Those skilled in the art will be capable of modifying the pretilt angle using the guidelines provided herein. In addition, as shown in Table 4, the electrooptical properties of photo-alignment materials made according to the present invention are equivalent to or superior to those alignment materials prepared using the rubbing process.

Therefore, as described above, according to the present invention, it is possible to provide a photo-alignment material useful in a liquid crystal alignment film in which the pretilt angle of the material is freely controllable, while providing a display quality equivalent or superior to the alignment materials that are made using a rubbing process.

While there have been illustrated and described what are considered to be preferred specific embodiments of the present invention, it will be understood by those skilled in the art that the present invention is not limited to the specific embodiments thereof, and that various changes and modifications and equivalents may be substituted for elements thereof without departing from the true spirit and scope of the present invention.

What is claimed is:

1. A photo-alignment material comprising a repeating unit represented by the following formula 1 and at least one repeating unit selected from the group consisting of structures represented by the following formula 8, wherein at least 20% by mole of the repeating units contain at least one photo-reactive functional group selected from the group consisting of structures represented by the following formula 5:

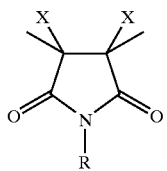

(1)

in which X is a hydrogen atom, fluorine atom, chlorine atom, or $C_{1\sim14}$ linear or branched alkyl group; Y is an oxygen atom or $C_{2\sim14}$ alkylene group; and R is a functional group having a structure represented by the following formula 3:

(3)

in which $R_1$ is selected from the group consisting of functional groups represented by the following formula 4; $R_2$ is selected from the group consisting of functional groups represented by the following formulas 5 and 6; $R_3$ is selected from the group consisting of functional groups represented by the following formula 7; k is an integer of from 0 to 3; l is an integer of from 0 to 5; and if there exist a plurality of $R_1$ or $R_2$, each $R_1$ or $R_2$ may be same or different:

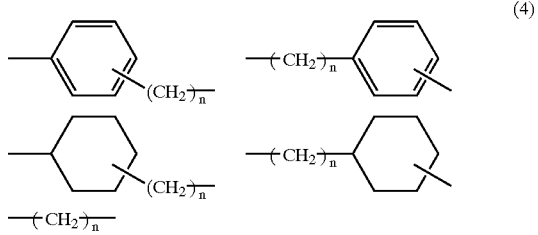

(4)

in which n is an integer of from 0 to 10,

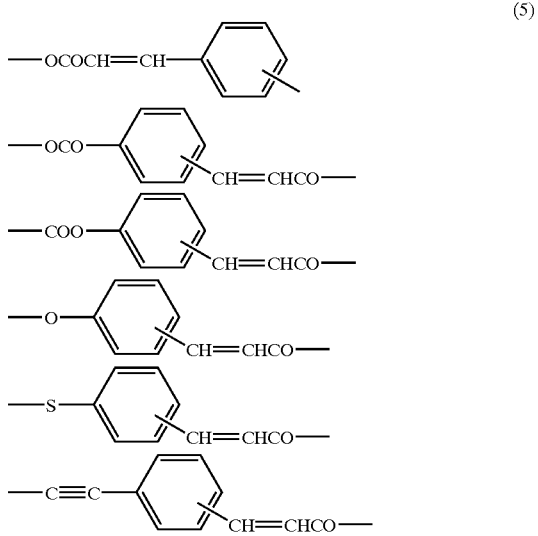

(5)

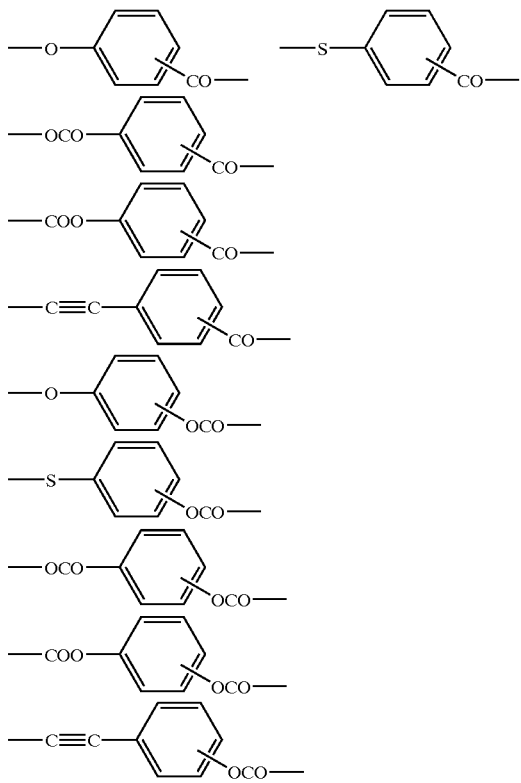

(6)

-continued

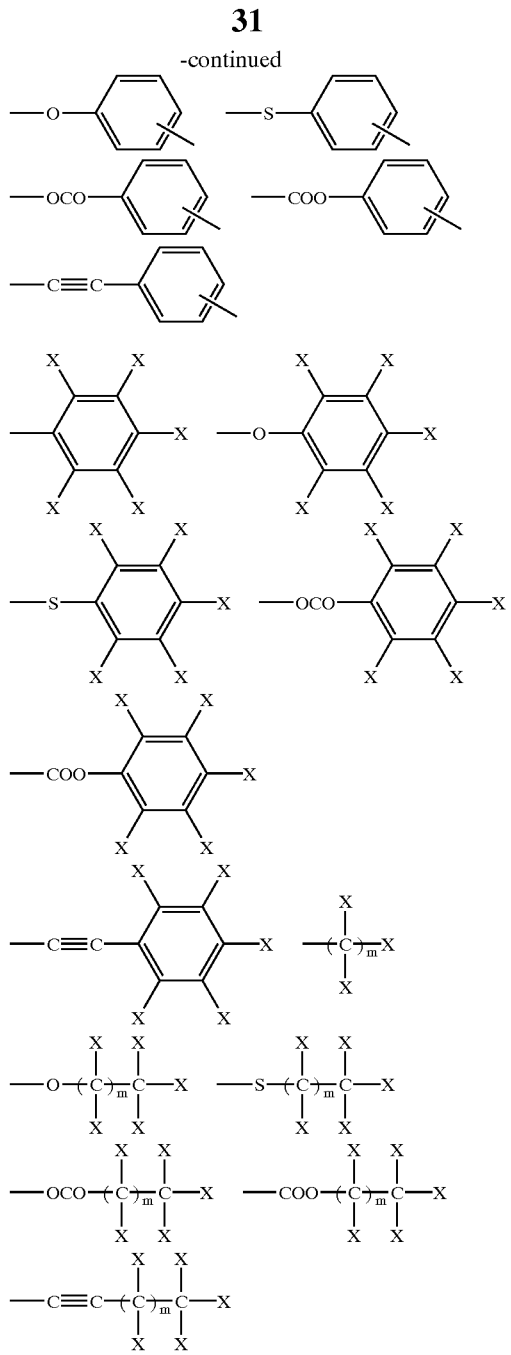

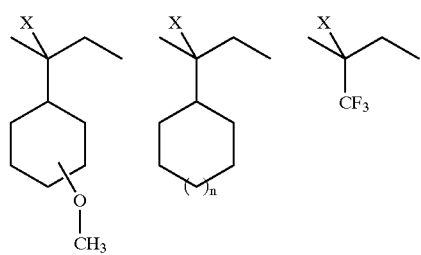

in which X in the groups represented by formula (7) is a hydrogen atom, fluorine atom, chlorine atom, $C_{1\sim 13}$ alkyl or alkoxy group, or —$(OCH_2)_pCH_3$ in which p is an integer of from 0 to 12, and m is an integer of from 0 to 18;

(8)

-continued

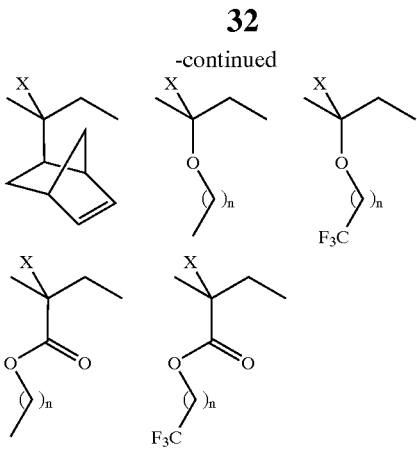

in which n is an integer of from 1 to 12.

2. A photo-alignment material comprising a repeating unit represented by the following formula 1, at least one repeating unit selected from the group consisting of structures represented by the following formula 2, and at least one repeating unit selected from the group consisting of structures represented by the following formula 8, wherein at least 20% by mole of the repeating units contain at least one photo-reactive functional group selected from group consisting of structures represented by the following formula 5:

(1)

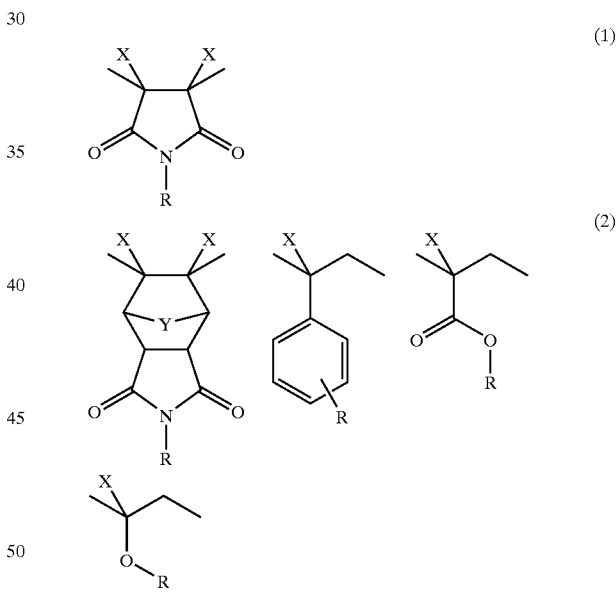

(2)

in which X is a hydrogen atom, fluorine atom, chlorine atom, or $C_{1\sim 14}$ linear or branched alkyl group; Y is an oxygen atom or $C_{2\sim 14}$ alkylene group; and R is a functional group having a structure represented by the following formula 3:

(3)

in which $R_1$ is selected from the group consisting of functional groups represented by the following formula 4; $R_2$ is selected from the group consisting of functional groups represented by the following formulas 5 and 6; $R_3$ is selected from the group consisting of functional groups represented by the following formula 7; k is an integer of from 0 to 3;

l is an integer of from 0 to 5; and if there exist a plurality of $R_1$ or $R_2$, each $R_1$ or $R_2$ may be same or different:
(4)
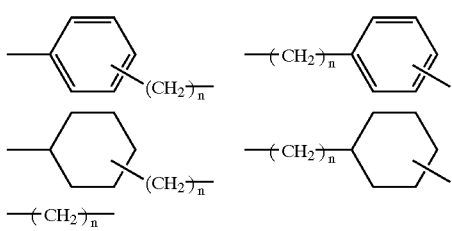
in which n is an integer of from 0 to 10,
(5)
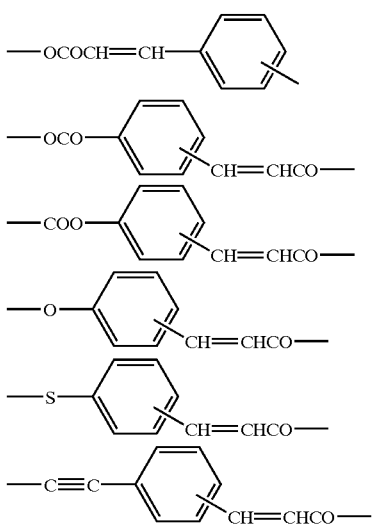
(6)
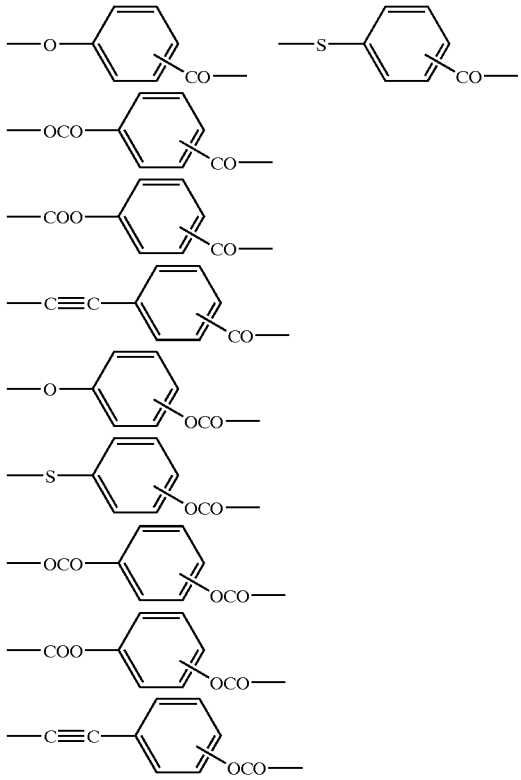
-continued
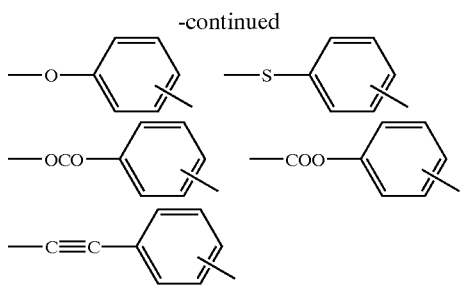
(7)
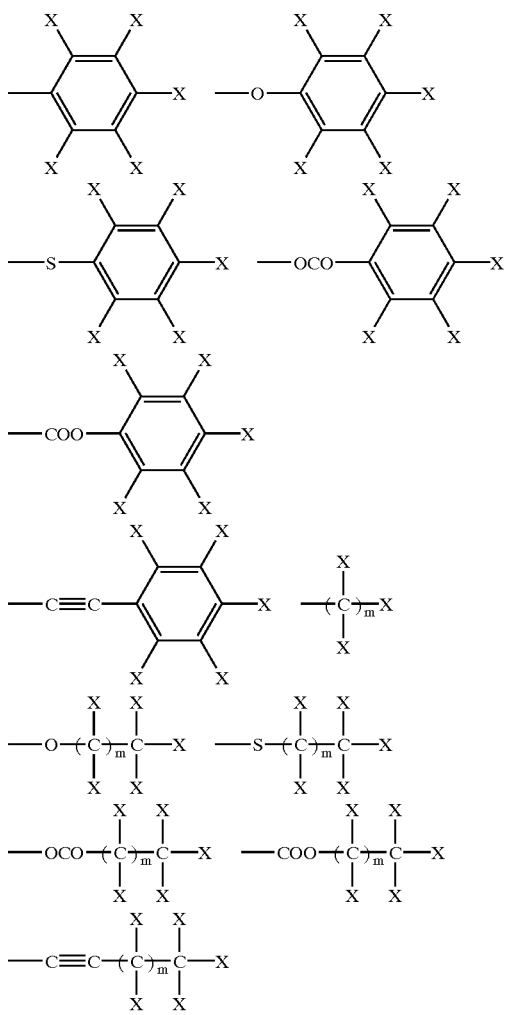
in which X in the groups represented by formula (7) is a hydrogen atom, fluorine atom, chlorine atom, $C_{1\sim13}$ alkyl or alkoxy group, or $-(OCH_2)_pCH_3$ in which p is an integer of from 0 to 12, and m is an integer of from 0 to 18;
(8)
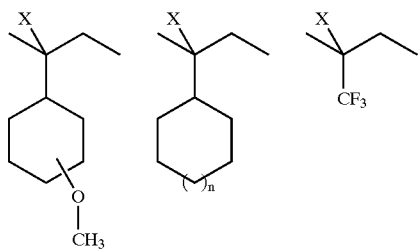

-continued

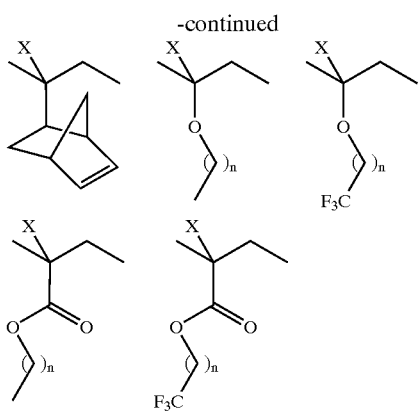

in which n is an integer of from 1 to 12.

3. The photo-alignment material according to claim 2, wherein the alignment material comprises a styrene-based repeating unit among the structures represented by the formula 2.

4. The photo-alignment material according to claim 1, wherein the alignment material comprises a cinnamate group as a photo-reactive group among the structures represented by the formula 5.

5. The photo-alignment material according to claim 2, wherein the alignment material comprises a cinnamate group as a photo-reactive group among the structures represented by the formula 5.

6. A liquid crystal alignment film comprising the photo-alignment material of claim 1.

7. A liquid crystal alignment film comprising the photo-alignment material of claim 2.

* * * * *